United States Patent
Schaeffer

(10) Patent No.: US 9,486,606 B2
(45) Date of Patent: Nov. 8, 2016

(54) SWAGED BRAIDED CATHETER AND METHOD OF FABRICATION

(71) Applicant: Cook Medical Technologies LLC, Bloomington, IN (US)

(72) Inventor: Darin G. Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/757,695

(22) Filed: Dec. 23, 2015

(65) Prior Publication Data

US 2016/0121075 A1    May 5, 2016

Related U.S. Application Data

(62) Division of application No. 13/383,306, filed as application No. PCT/US2010/041798 on Jul. 13, 2010, now Pat. No. 9,259,550.

(60) Provisional application No. 61/224,955, filed on Jul. 13, 2009.

(51) Int. Cl.
*A61M 25/00* (2006.01)

(52) U.S. Cl.
CPC ....... *A61M 25/005* (2013.01); *A61M 25/0012* (2013.01); *A61M 2025/0004* (2013.01); *A61M 2025/0059* (2013.01)

(58) Field of Classification Search
CPC .................. A61M 25/005; A61M 2025/0004; A61M 2025/0059
See application file for complete search history.

(56) References Cited

U.S. PATENT DOCUMENTS

| | | | |
|---|---|---|---|
| 2,407,929 A | 9/1946 | Jeckel | |
| 3,485,234 A | 12/1969 | Stevens | |
| 4,425,919 A | 1/1984 | Alston, Jr. et al. | |
| 4,472,216 A | 9/1984 | Högenhout et al. | |
| 4,547,193 A | 10/1985 | Rydell | |
| 4,665,604 A | 5/1987 | Dubowik | |
| 5,250,069 A | 10/1993 | Nobuyoshi et al. | |
| 5,358,493 A | 10/1994 | Schweich, Jr. et al. | |
| 5,465,710 A | 11/1995 | Miyagi et al. | |
| 5,695,469 A | 12/1997 | Segal | |
| 5,702,373 A | 12/1997 | Samson | |
| 5,704,926 A | 1/1998 | Sutton | |
| 5,755,704 A * | 5/1998 | Lunn | A61M 25/0012 600/585 |
| 6,042,578 A | 3/2000 | Dinh et al. | |
| 6,106,510 A | 8/2000 | Lunn et al. | |

(Continued)

FOREIGN PATENT DOCUMENTS

| | | |
|---|---|---|
| EP | 0 732 117 A2 | 3/1996 |
| EP | 1 712 247 A1 | 4/2006 |

*Primary Examiner* — Laura Bouchelle
*Assistant Examiner* — Melissa A Snyder
(74) *Attorney, Agent, or Firm* — Brinks Gilson & Lione

(57) ABSTRACT

A swaged braided catheter for use in various medical procedures is provided. The swaged braided catheter includes a tubular braid formed from a plurality of braided wire members. A plurality of intersections is formed by the braided wire members. The intersections are compressed defining a plurality of flattened regions along the tubular braid. The intersections have a first thickness before being compressed and a reduced second thickness after being compressed. The flattened regions with the reduced second thickness provide the swaged braided catheter with a reduced cross-sectional profile, and reduced catheter recoil.

8 Claims, 6 Drawing Sheets

(56) References Cited

U.S. PATENT DOCUMENTS

| | | |
|---|---|---|
| 7,297,302 B2 | 11/2007 | Berg et al. |
| 7,438,712 B2 | 10/2008 | Chouinard |
| 2002/0072729 A1 | 6/2002 | Hoste et al. |
| 2003/0145915 A1 | 8/2003 | Shimada |
| 2004/0024416 A1* | 2/2004 | Yodfat ............... A61F 2/01 606/200 |
| 2004/0143239 A1 | 7/2004 | Zhou et al. |
| 2006/0111649 A1* | 5/2006 | Zhou ............. A61M 25/0012 600/585 |
| 2007/0276354 A1 | 11/2007 | Osborne |

\* cited by examiner

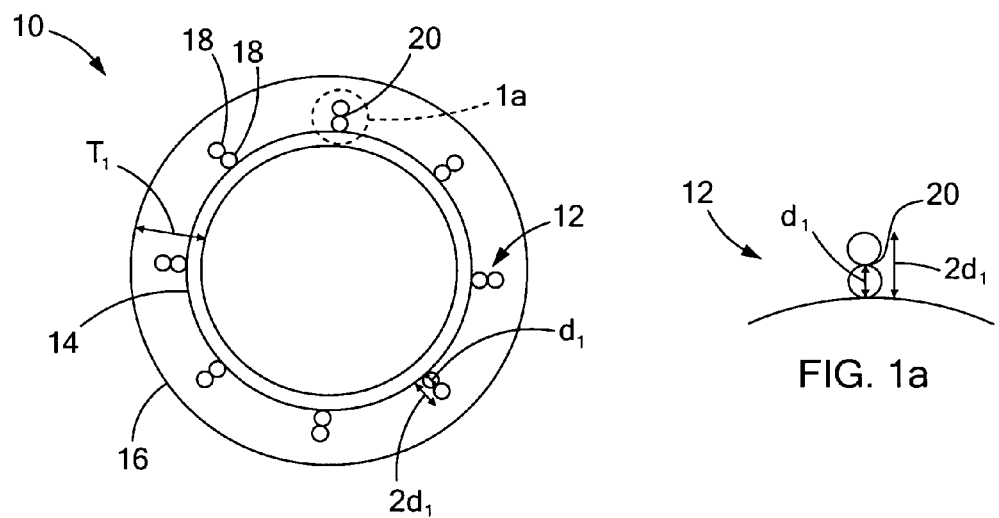
FIG. 1 Prior Art
FIG. 1a
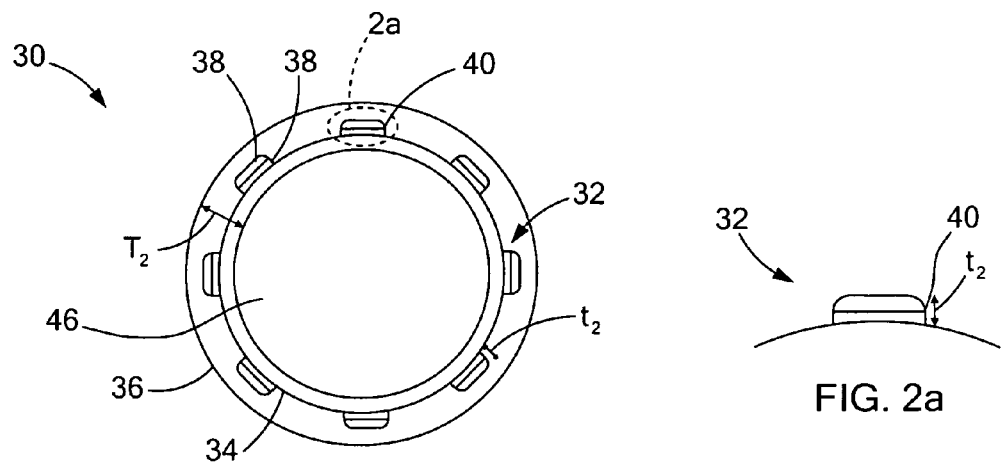
FIG. 2
FIG. 2a

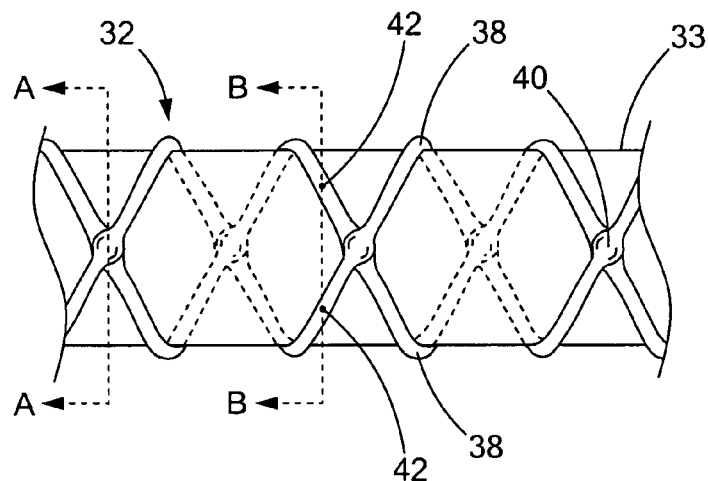
FIG. 3
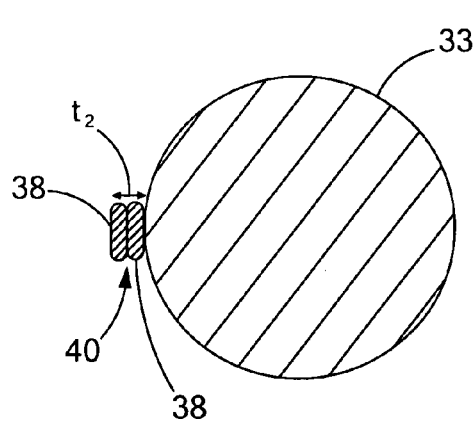 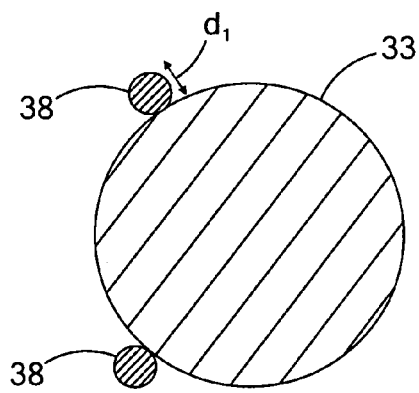
FIG. 3a  FIG. 3b

SWAGED BRAIDED CATHETER AND METHOD OF FABRICATION

CROSS-REFERENCE TO RELATED APPLICATIONS

This application is a divisional application of U.S. patent application Ser. No. 13/383,306, filed Jan. 10, 2012, which application is a 371 National of and claims the benefit of priority to PCT/US2010/041798, filed on Jul. 13, 2010 which application claims priority to U.S. Provisional Patent Application Ser. No. 61/224,955, filed Jul. 13, 2009, entitled "SWAGED BRAIDED CATHETER AND METHOD OF FABRICATION," the entire contents of which are incorporated herein by reference in their entirety.

BACKGROUND OF THE INVENTION

1. Field of Invention

The present invention relates to medical devices. More particularly, the invention relates to intravascular catheters incorporating a tubular braid.

2. Background

The use of intravascular catheters for treatment of the body is well known in the field of medicine. The need for a choice of catheter sizes and types has grown rapidly as the techniques for their use have been greatly improved and the types of medical uses have expanded quickly. One such catheter is a guide catheter which includes a tubular member having a lumen therethrough. Guide catheters are commonly used in diagnostic and treatment techniques related to vascular disease such as angioplasty. A guide catheter is inserted into the femoral artery and routed to a location near a treatment or diagnostic site through the aorta over the aortic arch to the ostium of a target vessel. The guide catheter provides a conduit so that fluid or another medical device can be delivered easily to the proximate location of treatment via the lumen of the guide catheter.

Prior art catheters often comprise a tubular member including a pair of congruent tubes, the inner one defining the lumen. Flexibility is an essential part of the catheter so that it may be successfully torqued, pushed and pulled on its way through the vascular passage to the desired site in the body. For control of the catheter and to prevent its kinking from excessive flexing a certain amount of rigidity is also required. The prior art catheters often meet this need for rigidity by adding a support member between the two tubes. This support member may comprise a braid of metal wire wrapped around the inner tube, and often imbedded within the outer tube.

One problem that has arisen is that as it becomes desirable to increase the diameter of the catheter lumen, it also becomes desirable to decrease the thickness of the walls of the tubes that form the catheter. However, it has been found that in thinner-walled catheters it is more difficult to prevent the kinking of the catheter.

In view of the above, it is apparent that there exists a need for an improved intravascular catheter.

BRIEF SUMMARY OF THE INVENTION

The present invention provides an improved intravascular catheter for use in various medical procedures and a method of fabricating the intravascular catheter.

In one embodiment, the catheter includes a tubular braid having a proximal end a distal end. The tubular braid includes a plurality of wire members braided together and a plurality of crossing points defined by crossing wire members of the braided wire members. The crossing points are compressed to define a plurality of flattened regions along the tubular braid. The crossing points have an initial first thickness before being compressed and a second thickness after being compressed. The second thickness is less than the first thickness.

In another embodiment, the catheter includes a tubular braid having a proximal end and a distal end. The tubular braid includes a plurality of braided wire members and a plurality of intersections formed by the braided wire members. The intersections are compressed to define a plurality of flattened regions along the tubular braid. The catheter further includes an inner liner positioned coaxially within and in contact with the tubular braid and an outer sleeve positioned coaxially about and in contact with the tubular braid. The inner liner defines a lumen of the catheter formed through the proximal and distal ends of the tubular braid.

The present invention also includes a method of forming a catheter. The method includes braiding a plurality of wire members to form a tubular braid having a proximal end and a distal end and a lumen formed through the proximal and distal ends. The tubular braid includes a plurality of intersections formed by the braided wire members. The plurality of intersections has a first thickness. The method further includes swaging the tubular braid to compress the plurality of intersections to a second thickness less than the first thickness. The compressed intersections define a plurality of flattened regions along the tubular braid.

Further objects, features, and advantages of the present invention will become apparent from consideration of the following description and the appended claims when taken in connection with the accompanying drawings.

BRIEF DESCRIPTION OF THE DRAWINGS

FIG. 1 is an end view of a braided catheter commonly known in the art;

FIG. 1a is an enlarged view of circle 1a of FIG. 1;

FIG. 2 is an end view of a swaged braided catheter in accordance with an embodiment of the present invention;

FIG. 2a is an enlarged view of circle 2a of FIG. 2;

FIG. 3 is a perspective view of a tubular braid positioned about a mandrel in accordance with an embodiment of the present invention;

FIG. 3a is a cross-sectional view taken along line A-A in FIG. 3;

FIG. 3b is a cross-sectional view taken along line B-B in FIG. 3;

DETAILED DESCRIPTION OF THE INVENTION

Figure 4:
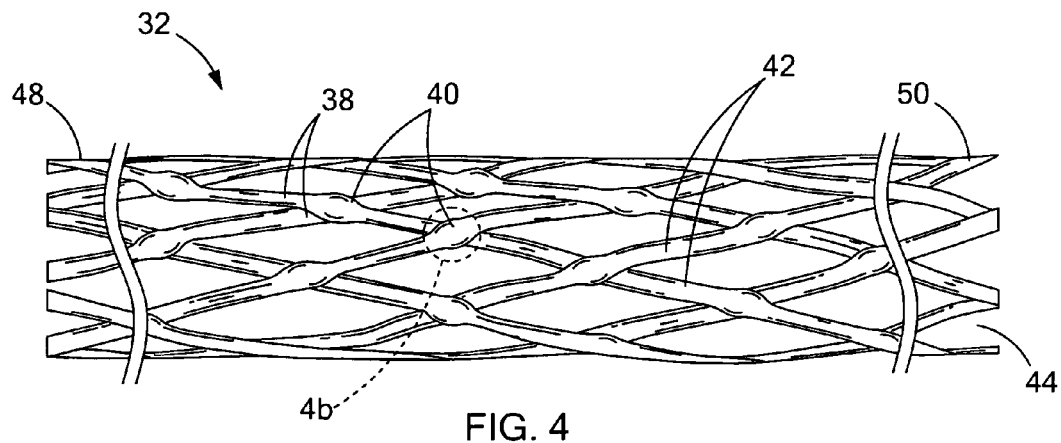
FIG. 4 is a perspective view of a tubular braid in accordance with an embodiment of the present invention.

The following provides a detailed description of currently preferred embodiments of the present invention. The description is not intended to limit the invention in any manner, but rather serves to enable those skilled in the art to make and use the invention.

Referring now to FIG. 1, a braided shaft or catheter found in the prior art is denoted by reference numeral 10. The braided catheter 10 generally includes a tubular braid 12, an inner jacket or liner 14, and an outer sleeve or jacket 16. The tubular braid 12 includes a plurality of filaments or wire strands 18 braided together forming a plurality of crossing points or intersections 20. Accordingly, the braided catheter 10 has a wall thickness which is equal to the sum of: the thickness $2d_1$ of the tubular braid 12, i.e., the thickness of the intersections 20 or twice the diameter $d_1$ of each of the crossing wire strands 18; the thickness of the inner liner 14; and the thickness of the outer jacket 16 extending beyond the tubular braid 12.

As opposed to coiled shafts or catheters commonly known in the art, braided catheters, such as the one described above with respect to FIG. 1, have a greater cross-sectional profile, or wall thickness, due to the overlapping of the wire strands 18 during braiding of the tubular braid (i.e., due to the thickness of the intersections 20). Embodiments of the present invention provide a swaged braided catheter having a reduced cross-sectional profile, or wall thickness, as well as reduced catheter recoil. In addition, embodiments of the present invention may provide a swaged braided catheter with increased torqueability.

FIG. 2 illustrates a swaged braided shaft or catheter 30 in accordance with a preferred embodiment of the present invention. The swaged braided catheter 30 generally includes a tubular braid 32, an inner jacket or liner 34, and an outer sleeve or jacket 36. The tubular braid 32 includes a plurality of filaments or wire strands 38 braided together. The wire members or strands 38 preferably have an initial round cross-section with a thickness or diameter $d_1$ along their lengths, similar to the wire strands 18 in FIG. 1. As illustrated in FIG. 2, the wire strands 38 cross each other forming a plurality of crossing points or intersections 40 which are compressed or flattened to a thickness $t_2$, which is less than the thickness $2d_1$ of the prior art tubular braid 12. Preferably, the thickness $t_2$ of the compressed intersections 40 is approximately equal to the initial diameter $d_1$ of an individual wire strand 38. Accordingly, the swaged braided catheter 30 has a wall thickness $T_2$, which is equal to the sum of: the thickness of the tubular braid 32, i.e., the thickness $t_2$ of the flattened intersections 40; the thickness of the inner liner 34; and the thickness of the outer jacket 36 extending beyond the tubular braid 32.

In this embodiment, the intersections 40 of the tubular braid 32 initially have a thickness $2d_1$ equal to twice the diameter $d_1$ of the crossing wire strands 38 similar to the intersections 20 of the prior art tubular braid 12 shown in FIGS. 1 and 1a. As best illustrated in FIG. 2a, the tubular braid 32 is swaged (discussed in further detail below) and includes flattened intersections 40. In this embodiment, the intersections 40 are flattened to a thickness $t_2$, which is preferably approximately equal to $d_1$, i.e., preferably about half the initial thickness $2d_1$ of the pre-compressed intersections 40.

Preferably, the tubular braid 32 is formed from, for example, stainless steel wire strands 38. Although high tensile stainless steel, such as 304V stainless steel wire, is preferred, other suitable materials, including metals and metal alloys, such as tungsten, gold, titanium, silver, copper, platinum, palladium, iridium, ELGILOY nickel-cobalt alloys, cobalt chrome alloys, molybdenum tungsten alloys, tantalum alloys, titanium alloys, and any other suitable material known in the art used in forming braided catheters. The wire strands 38 preferably have an initial round cross-section with a thickness or diameter $d_1$ between about 0.0010 inches and about 0.0050 inches, preferably about 0.002 inches. The term "braid" refers to tubular constructions in which the wire strands 38 are woven in an in-and-out fashion as they cross to form a tubular member defining a single lumen 44 formed through proximal and distal ends 48 and 50 of the tubular braid 32 (FIG. 4). The tubular braid 32 may be made up of a suitable number of wire strands 38, typically six, eight, twelve, sixteen, twenty-four, twenty-eight, or more.

The tubular braid 32 may be formed through any conventional braiding technique known by those skilled in the art. The wire strands 38 may be braided in a 1 over 1 pattern, a 2 over 2 pattern, or any other suitable braid pattern in which the wire strands 38 are woven together forming a plurality of intersections 40. The pic and other characteristics of the tubular braid 32 will be selected to provide the desired stretch and flexibility for the swaged braided catheter 30. Usually, the pic will be in the range from around 20 to around 150 pics/inch, preferably from around 40 to around 80 pics/inch, and the pic may be constant over the entire length of the tubular braid 32 or may be varied to increase flexibility at or near the distal end 50 of the swaged braided catheter 30. In particular, the tubular braid 32 characteristics such as the pic, cross-sectional area, material strength, and the like, may be varied to vary the flexibility in the swaged braided catheter 30. The tubular braid 32 may have a pitch angle from about 20 degrees to about 70 degrees.

After the tubular braid 32 is formed, it is swaged to compress or flatten the intersections 40. Referring to FIG. 3, the tubular braid 32 is preferably positioned over a swage die core or rigid mandrel 33. The mandrel 33 and tubular braid 32 are passed through a swage die, thereby flattening the tubular braid 32 at each intersection 40 as shown in FIG. 3. The swage die is sized to compress the intersections 40 of the tubular braid 32 such that as the tubular braid 32 is passed through the swage die the intersections 40 are flattened between the swage die and the mandrel 33 positioned within the lumen 44 of the tubular braid 32, i.e., by the opposing compression forces exerted upon the intersections 40 via the swage die and the mandrel 33.

As illustrated in FIG. 3a, the wire strands 38 are flattened at the intersections 40 defining a thickness $t_2$ at the intersections 40. As shown in FIG. 3b, the wire strands 38 maintain their initial round cross-section of diameter $d_1$ at a location 42 between the intersections 40. It is noted, however, that during swaging, the regions of the wire strands 38 immediately adjacent the intersections 40 may become compressed as well, but not to the same degree as the intersections 40. Thus, the thickness of the wire strands 38 immediately adjacent the intersections 40 may be less than the initial thickness or diameter $d_1$ of the wire strands 38 before swaging. This is because the greatest cross-sectional profile of the tubular braid 32 is at the intersections 40 due to the overlapping wire strands 38. Accordingly, portions of the wire strands 38 in between the intersections 40 preferably maintain the initial round cross-section with a thickness or diameter $d_1$. For example, portions of the wire strands 38 located about midway between the intersections 40 (e.g., midpoints 42 in FIG. 3) likely maintain a round cross-section with a diameter $d_1$, as best illustrated in FIG. 3b.

Figure 4A:
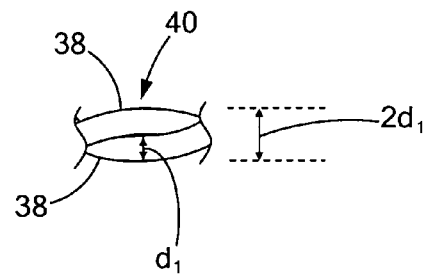
FIG. 4a is an enlarged side view of a pre-compressed intersection of the tubular braid of FIG. 4.

FIG. 4 is a perspective view of a swaged tubular braid 32 having flattened intersections 40 in accordance with the teachings of the present invention. Referring to FIG. 4a, a side view of an intersection 40 of the tubular braid 32 prior to being flattened, i.e., before being passed through the swage die, is illustrated. As shown in FIG. 4a, the wire strands 38 forming the tubular braid 32 have an initial round cross-section with a diameter $d_1$. Accordingly, the thickness $2d_1$ of the intersections 40 is equal to twice the diameter $d_1$ of the wire strands 38.

Figure 4B:
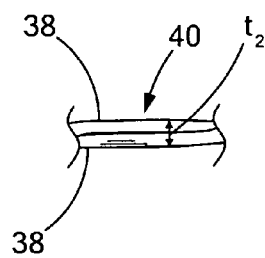
FIG. 4b is an enlarged side view of section 4b of FIG. 4.

Referring to FIG. 4b, a side view of the intersection 40 in circle 4b of FIG. 4 is illustrated. Thus, FIG. 4b illustrates a side view of a flattened intersection 40 of the tubular braid 32 after being swaged, i.e., after being passed through the swage die. As shown in FIG. 4b, the wire strands 38 at the intersections 40 have been flattened and compressed together, thus altering the initial round cross-section of diameter $d_1$. In this embodiment, the compression force of the swage die alters the initial round cross-section of the wire strands 38 to a substantially rectangular cross-section with a thickness, or height, less than the diameter $d_1$, preferably about half the diameter $d_1$. Accordingly, the thickness $t_2$ of the flattened intersections 40 after swaging is less than the thickness $2d_1$ of the intersections 40 before swaging, and is preferably about half the thickness $2d_1$ of the intersections 40 before swaging, i.e., the thickness $t_2$ of the flattened intersections 40 is preferably about the same as the initial thickness or diameter $d_1$ of a single wire strand 38 prior to swaging.

It should be noted that the tubular braid 32 may be swaged to different degrees, i.e., the diameter of the swage die may be smaller or larger according to the desired degree of swaging. While it is preferred that the thickness of the intersections 40 is reduced by about half after swaging the tubular braid 32, the reduction in thickness of the intersections 40, and thus the cross-sectional profile of the tubular braid 32 may be greater or lesser depending on the degree of swaging (i.e., depending on the dimensions of the swage die in comparison to the greatest outer diameter of the tubular braid 32) and/or the number of times the tubular braid 32 is passed through the swage die.

Preferably, the swaged braided catheter 30 includes an inner liner 34, as illustrated in FIG. 2. The inner liner 34 is typically a tubular sleeve, formed of a polymeric material, disposed within the lumen 44 of the tubular braid 32, thus defining the inner lumen 46 of the swaged braided catheter 30. The lumen 46 defined by the inner liner 34 can provide passage to a variety of different medical devices or fluids, and thus the inner liner 34 can be manufactured from or include a lubricious material to reduce friction within the lumen 46. Preferably, the inner liner 34 is formed from a lubricious polymer, such as a fluorocarbon (e.g., polytetrafluoroethylene (PTFE)), a polyamide (e.g., nylon), a polyolefin, a polyimide, or the like. Additional polymeric materials which may make up the inner liner 34 include polyethylene, polyvinyl chloride (PVC), ethyl vinyl acetate (EVA), polyethylene terephthalate (PET), and their mixtures and copolymers. Another useful class of polymers is thermoplastic elastomers, including those containing polyesters as components. For example, the inner liner 34 may be formed by extruding a rigid thermoplastic elastomer polymer such as polyamide polyether block copolymer (Pebax®). The inner liner 34 can be dimensioned to define a lumen 46 having an appropriate inner diameter to accommodate its intended use.

Preferably, the inner liner 34 defines a lumen 46 having a diameter in the range of about 0.01 inches to about 0.375 inches and has a wall thickness of about 0.001 inches to about 0.01 inches. The tubular braid defines a lumen 44 having a diameter approximately equal to the outer diameter of the inner liner 34. Thus, the inner diameter of the tubular braid 32 is preferably in the range of between about 0.012 inches to about 0.395 inches. The greatest thickness of the tubular braid 32 is at the intersections 40 having a thickness $t_2$. Since the thickness $t_2$ is less than $2d_1$ (twice the diameter $d_1$ of the crossing wire strands 38 at the intersections 40), and preferably approximately equal to the initial diameter $d_1$ of a single wire strand 38, the greatest thickness $t_2$ of the tubular braid 32 is in the range of about 0.001 inches to about 0.008 inches.

Preferably, the swaged braided catheter 30 further includes a polymeric outer jacket 36. As shown in FIG. 2, a polymeric material is extruded over the top of the inner liner 34 and tubular braid 32 to form the outer jacket 36. In this embodiment, the tubular braid becomes embedded within the outer jacket 36 and the outer jacket 36 bonds with inner liner 34. As illustrated in FIG. 2, contact regions between the outer jacket 36 and the inner liner 34 are shown in the interstices between the open weave (i.e., between the intersections 40) of the tubular braid 32. Although the open area between intersections 40 of the tubular braid 32 is not absolutely necessary as a means of allowing contact between the inner liner 34 and the outer jacket 36, such is quite desirable. Furthermore, in embodiments in which the outer jacket 36 is placed on the outer surface of tubular braid 32 by dipping the tubular braid 32 and inner liner 34 into a molten or latex liquid, the contact is inevitable.

The outer jacket 36 can be composed of a variety of materials, preferably a soft thermoplastic material having a hardness in the range from about 30 A to about 74 D. Exemplary materials include Pebax®, polyurethanes, silicone rubbers, nylons, polyethylenes, fluorinated hydrocarbon polymers, and the like. If a section with even more flexibility is desired, the outer jacket 36 may also be of a member selected from a more flexible material such as low density polyethylene (LDPE), polyvinylchloride, THV, etc. and other polymers of suitable softness or a modulus of elasticity. Preferably, the outer jacket 36 has an inner diameter that is slightly greater than the inner liner 34 and accommodates the thickness of the tubular braid 32. The outer jacket 36 preferably has a thickness in the range of about 0.001 inches to about 0.008 inches.

The outer jacket 36 may include a lubricious material, or the swaged braided catheter 30 may include a coating layer, such as a lubricious coating layer, over part or all of the swaged braided catheter 30 (i.e., over part or all of the outer surface of the outer jacket 36). Suitable lubricious polymers are well known in the art and can include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It is noted that swaged braided catheters having a swaged tubular braid in accordance with teachings of the present invention, but lacking an inner liner or an outer jacket, also fall within the scope of the present invention.

Figure 5A:
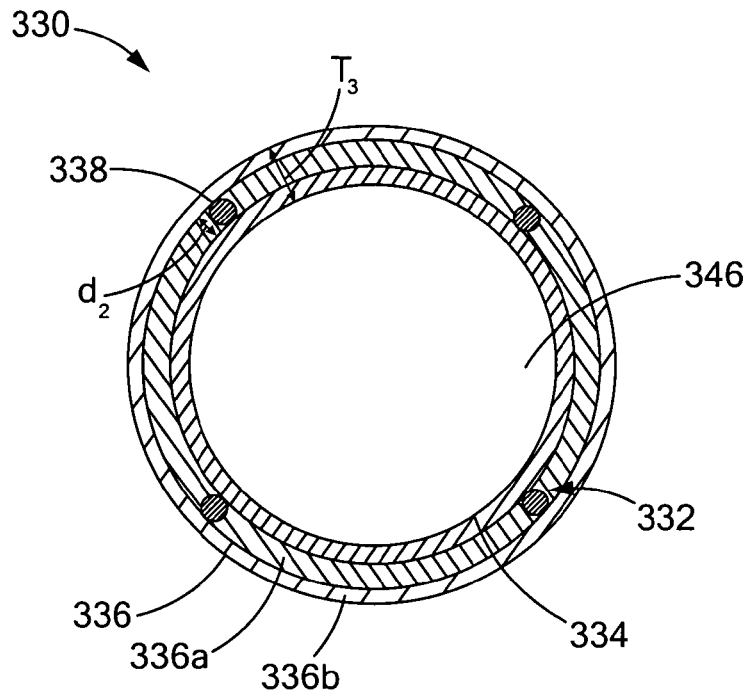
FIG. 5a is a cross-sectional view of a swaged braided catheter in accordance with another embodiment of the present invention, the cross-section taken along a portion of the catheter in which the wire strands of the tubular braid do not cross one another.
Figure 5B:
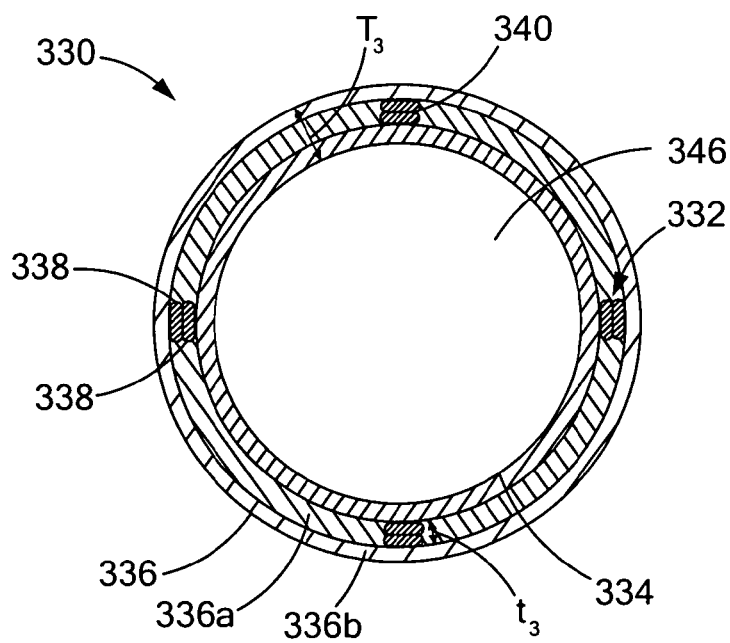
FIG. 5b is a cross-sectional view of the swaged braided catheter of FIG. 5a, the cross-section taken along a different portion of the catheter in which the wire strands of the tubular braid cross one another.

FIGS. 5a-b depict an embodiment of a swaged braided catheter 330 in accordance with the teachings of the present invention and having a description similar to that of FIG. 2, and in which similar components are denoted by similar reference numerals increased by 300. In this embodiment, the outer jacket 336 includes a first polymeric material layer 336a which is extruded to form an outer jacket tubing of appropriate size and thickness and then slipped over the combination of the inner liner 334 and the tubular braid 332. The first polymeric material layer 336a may include polyurethanes, silicone rubbers, nylons, polyethylenes, fluoronated hydrocarbon polymers, and the like. Alternatively, the first polymeric material layer 336a may include a more flexible material, such as low density polyethylene (LDPE), polyvinylchloride, THV, etc. and other polymers of suitable softness or a modulus of elasticity. In this embodiment, the extruded outer jacket tubing, i.e., the first polymeric material layer 336a is heat shrunk into place using a second polymeric layer 336b, preferably Pebax®. Preferably, the second polymeric layer 336b shrinks down to the top of the tubular braid 332 and the filler material, i.e., the first polymeric layer 336a, fills in between the interstices of the tubular braid 332.

As illustrated in FIG. 5a, the wire strands 338 preferably have a round cross-section with a diameter $d_2$. The wire strands 338 cross each other forming a plurality of crossing points or intersections 340 having an initial thickness $2d_2$ equal to twice the diameter or $d_2$ of the overlying wire strands 338. The intersections 340 are compressed or flattened to a thickness $t_3$, as illustrated in FIG. 5b. The thickness $t_3$ of the flattened intersections 340 of the swaged tubular braid 332 is less than the thickness $2d_2$ of the tubular braid 332 before swaging, i.e., the thickness of crossing wire members 338 with an initial diameter $d_2$. The thickness $t_3$ of the flattened intersections 340 is preferably approximately equal to the initial thickness or diameter $d_2$ of an individual wire strand 338. Accordingly, the swaged braided catheter 330 has a wall thickness $T_3$, which is equal to the sum of: the thickness of the tubular braid 332, i.e., the thickness $t_3$ of the flattened intersections 340; the thickness of the inner liner 334; and the thickness of the second polymeric layer 336b of the outer jacket 336.

Thus, comparing the prior art embodiment of FIG. 1 with the embodiments of FIGS. 2 and 5a-b, assuming the thickness of the inner liner is kept constant, as well as the thickness the outer jacket extends beyond the tubular braid in FIG. 2, or the thickness of the second polymeric layer in FIGS. 5a-b, a swaged braided catheter incorporating a swaged tubular braid in accordance with embodiments of the present invention has a reduced wall thickness ($T_2$ in FIG. 2 and $T_3$ in FIGS. 5a-b) when compared with the wall thickness ($T_1$) of a braided catheter incorporating a tubular braid of the prior art (FIG. 1).

In addition to providing reduced wall thickness, swaged braided catheters incorporating a swaged tubular braid with flattened intersections 40 in accordance with the teachings of the present invention provide reduced catheter recoil.

Increased torqueability is also likely with the swaged braided catheters of the present invention. This is due to the interlocking of the wire strands at the intersections that occurs after the tubular braid is swaged. The compression force exerted on the intersections during swaging flattens the wire strands and compresses them together forming a tighter fit between the wire strands along the flattened intersections. This, in turn, reduces the catheter recoil and likely increases torqueability of the swaged braided catheter.

Figure 6:
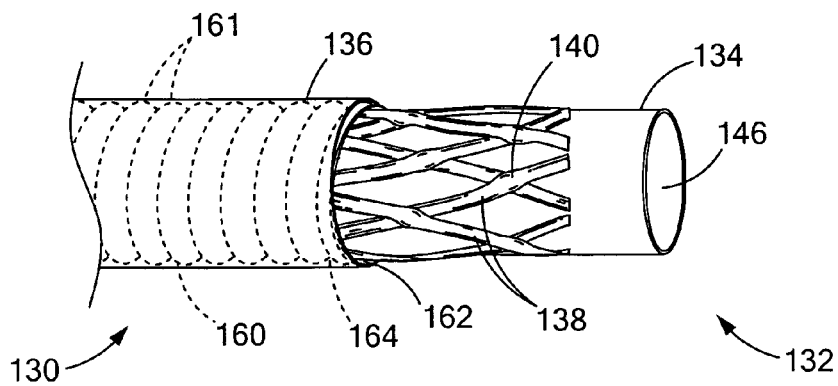
FIG. 6 is a partially cut-away perspective view of a swaged braided catheter in accordance with another embodiment of the present invention.

FIG. 6 depicts an embodiment of a swaged braided catheter 130 in accordance with further embodiments of the present invention and having a description similar to that of FIGS. 2 and 4, and in which similar components are denoted by similar reference numerals increased by 100. In this embodiment, the swaged braided catheter 130 includes an outer coil shaft 160 commonly known and used in a variety of medical applications by those skilled in the art. The outer coil shaft 160 has a proximal end (not shown) and a distal end 164 and a lumen 162 formed therethrough. The lumen 162 is dimensioned to receive the tubular braid 132. Preferably, the tubular braid 132 includes an inner liner 134, which defines the inner lumen 146 of the swaged braided catheter 130.

In this embodiment, the outer coil shaft 160 is positioned directly over the tubular braid 132, although there may be a polymeric liner material disposed between the tubular braid 132 and the outer coil shaft 160. An outer jacket 136 is preferably disposed about the outer coil shaft 160. In this embodiment, the outer jacket 136 is preferably heat shrunk about the outer coil shaft 160. The outer jacket 136 may join with the inner liner 134 through gaps (not shown) between coil turns 161 and the interstices of the tubular braid 32. For illustration purposes, the tubular braid 132 is shown extending distally from the outer coil shaft 160 and the outer jacket 136, and the inner liner 134 is shown extending distally from the tubular braid 132, however, the distal ends of the outer jacket 136 and the outer coil shaft 160, the tubular braid 132, and the inner liner 134 are preferably commonly aligned with one another.

Figure 7:
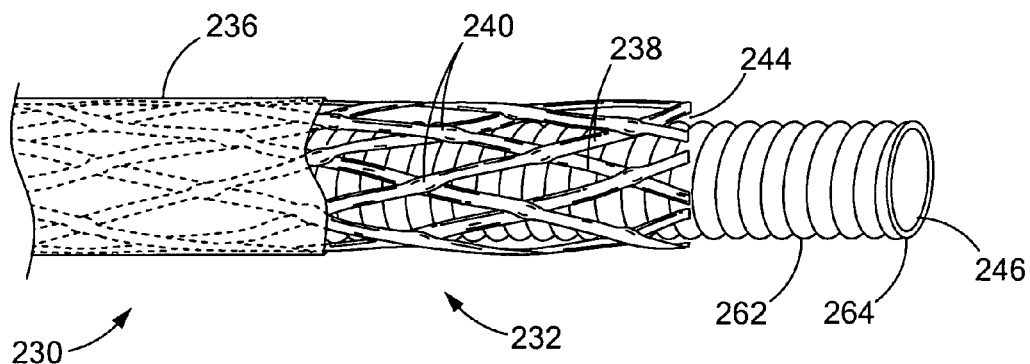
FIG. 7 is a partially cut-away perspective view of a swaged braided catheter in accordance with yet another embodiment of the present invention.

FIG. 7 depicts an embodiment of a swaged braided catheter 230 in accordance with further embodiments of the present invention and having a description similar to that of FIGS. 2 and 4, and in which similar components are denoted by similar reference numerals increased by 200. In this embodiment, the swaged braided catheter 230 includes an inner coil shaft 262 commonly known and used in a variety of medical application by those skilled in the art. The inner coil shaft 262 has a proximal end (not shown) and a distal end 264 and a lumen 246 formed therethrough, defining the inner lumen 246 of the swaged braided catheter 230. The tubular braid 232 is dimensioned to receive the inner coil shaft 262 and the inner coil shaft 262 can be dimensioned to define a lumen 246 having an appropriate inner diameter to receive a variety of medical devices to accommodate the intended use of the swaged braided catheter 230. In this embodiment, an outer jacket 236 is disposed over the tubular braid 232.

For illustration purposes, the tubular braid 232 is shown extending distally from the outer jacket 236, and the inner coil shaft 262 is shown extending distally from the tubular braid 232, however, the distal ends of the outer jacket 236, the tubular braid 232, and the inner coil shaft 262 are preferably commonly aligned with one another. As illustrated in FIG. 7, the tubular braid 232 is positioned directly over the inner coil shaft 262. Alternatively, the tubular braid 232 may include an inner liner, similar to that shown and described with respect to FIG. 2, which is dimensioned to receive the inner coil shaft 262. The inner coil shaft 262 may include an inner liner similar to that described and shown in FIG. 2, thus defining the inner lumen 246 of the braided catheter 230.

The composition of the outer coil shaft 160 of FIG. 6 and the inner coil shaft 262 of FIG. 7 may be of any of the materials listed above for use in constructing the tubular braid. Additional exemplary materials include superelastic alloys, such as nitinol, and radiopaque metals and alloys, for example, platinum alloys.

It is also within the scope of the present invention for a swaged braided catheter in accordance with embodiments of the present invention to include both an inner coil shaft coaxially positioned within the lumen of the tubular braid and an outer coil shaft coaxially positioned about, or encapsulating, the tubular braid such that the tubular braid is a layer in between the outer and inner coils of the swaged braided catheter. In this embodiment, an inner liner may be disposed between the tubular braid and the outer coil shaft and/or between the tubular braid and the inner coil shaft.

Figure 8:
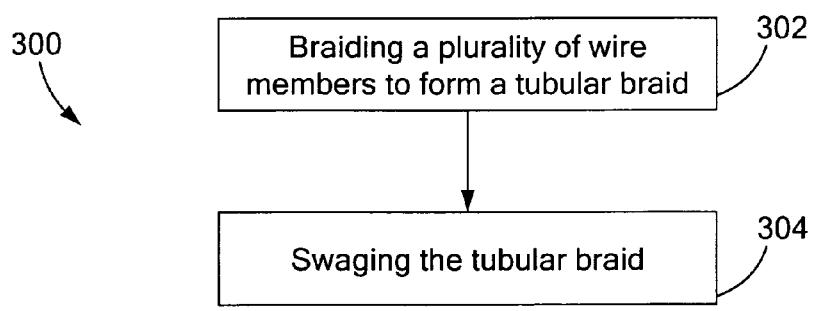
FIG. 8 is a flow chart illustrating a method of fabricating a braided catheter in accordance with an embodiment of the present invention.
Figure 9:
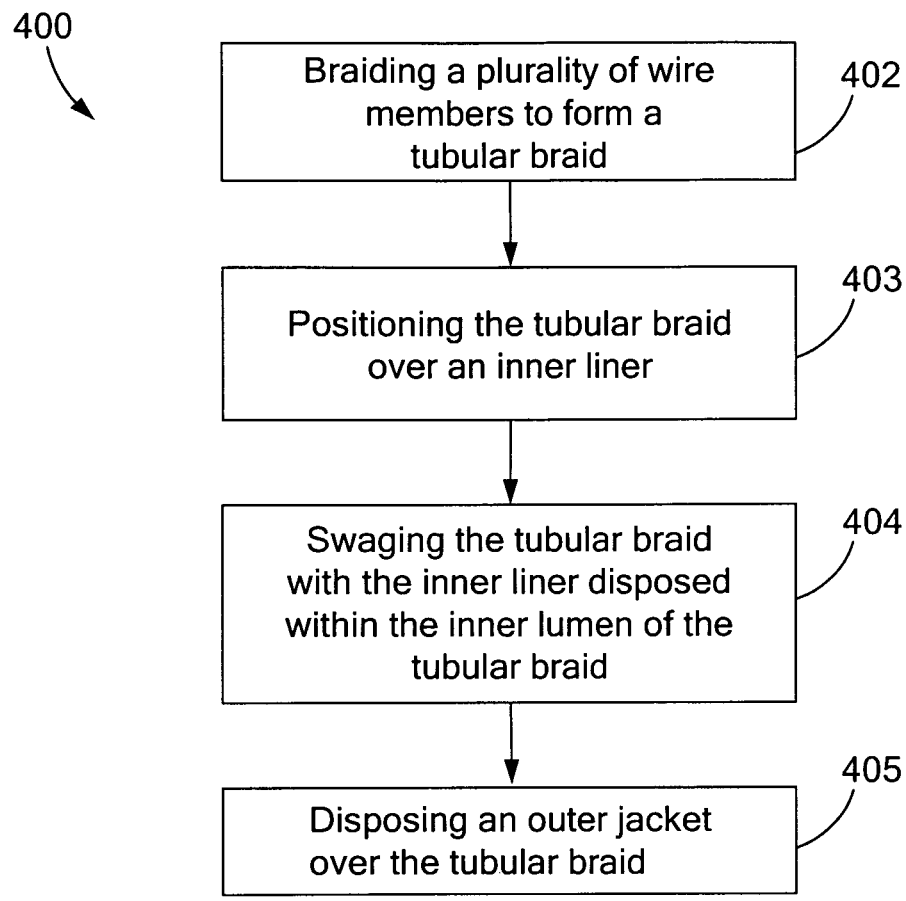
FIG. 9 is a flow chart illustrating a method of fabricating a braided catheter in accordance with another embodiment of the present invention.

Referring to FIGS. 8-9, methods of fabricating a swaged braided catheter 30 in accordance with embodiments of the present invention is provided. The method (300) of FIG. 8 includes braiding (302) a plurality of wire members or strands 38 to form a tubular braid 32 having a plurality of intersections 40 formed by overlying or crossing wire strands 38. The tubular braid 32 includes a proximal end 48 and a distal end 50 and a lumen 44 formed therethrough. The method (300) further includes swaging (304) the tubular braid 32 to compress or flatten the plurality of intersections 40 along the tubular braid 32. Swaging (304) the tubular braid 32 preferably includes disposing the tubular braid 32 over an inner swage core or mandrel 33 and passing the mandrel 33 and the tubular braid 32 through a swage die to compress the intersections 40 to form a plurality of flattened regions along the tubular braid 32.

In this example, the wire strands 38 may be braided together over the same mandrel 33 that is passed through the swage die with the tubular braid 32 such that the tubular braid 32 is formed over the mandrel 33 (i.e., the mandrel 33 is positioned within the lumen 44 of the tubular braid 32) at the start of fabrication. Alternatively, the tubular braid 32 may be formed and then disposed over the mandrel 33 prior to passing the mandrel 33 and the tubular braid 32 through the swage die.

Preferably, the tubular braid 32 is heat treated or annealed typically by exposure to flame or resistance heater to bring down the ultimate tensile strength of the material of the wire strands 38. This may be done before or after swaging the tubular braid 32, or it may be done in iterations (e.g., swage; anneal, swage, anneal) if a greater degree of swaging (e.g. by passing the tubular braid 32 through the swage die multiple times) is desired. This heat treatment step further prevents any loose ends at the proximal and distal ends 48, 50 of the tubular braid 32 after the ends are transversely cut to provide a clean cut at the proximal and distal ends 48, 50.

The tubular braid 32 is preferably coaxially positioned about an inner liner 34. The tubular braid 32 can be positioned over the inner liner 34 by axially compressing the tubular braid 32 to enlarge the inner diameter of the tubular braid 32 and permit easy positioning of the tubular braid 32 over the inner liner 34. Once the tubular braid 32 has been positioned over the inner liner 34, an outer jacket 36 is preferably positioned about the tubular braid 32 and the inner liner 34. The outer jacket 36 can be co-extruded over the tubular braid 32, it can be pre-formed and then heat shrunk into position, or it can be placed on the outer surface of the tubular braid 32 by dipping the tubular braid 32 and inner liner 34 into a molten or latex liquid. The outer jacket 36 may be applied to the outer surface of the tubular braid 32 through any other suitable means known by those skilled in the art.

FIG. 9 illustrates an alternative method (400) of fabricating a swaged braided catheter 30 in accordance with the teachings of the present invention. The method (400) of FIG. 9 includes braiding (402) a plurality of wire members or strands 38 to form a tubular braid 32 having a proximal end 48 and a distal end 50 and a lumen 44 formed therethrough. The tubular braid 32 includes a plurality of intersections 40 formed by overlying or crossing wire strands 38. The method (400) further includes positioning the tubular braid over an inner liner 34 formed by any well known means in the art, for example, by extrusion.

The steps of braiding (402) and positioning (404) may be combined in embodiments where the tubular braid 32 is actually braided over the inner liner 34 such that the inner liner 34 is disposed within the inner lumen 44 of the tubular braid 32, defining the inner lumen 46 of the swaged braided catheter 30. In this embodiment, if the tubular braid 32 is annealed, the inner liner 34 is preferably formed from a polymer with a higher melt temperature, such as polyaryletheretherketone (PEEK).

Alternatively, the tubular braid 32 can be braided and then positioned over the inner liner 34 by any means known in the art, for example, by axially compressing the tubular braid 32 to enlarge the inner diameter of the tubular braid 32 and sliding the tubular braid 32 over the inner liner 34. In this embodiment, the tubular braid 32 is preferably annealed prior to being positioned over the inner liner 34 to prevent the inner liner 34 from melting.

Figure 10:
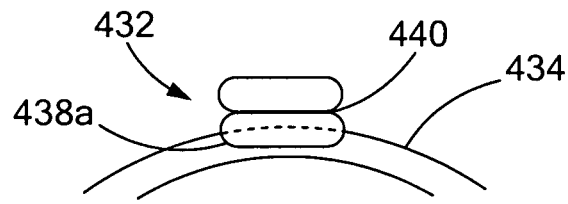
FIG. 10 is an enlarged view of an intersection of a swaged tubular braid of a swaged braided catheter in accordance with yet another embodiment of the present invention.

The method (400) of FIG. 9 further includes swaging (404) the tubular braid with the inner liner disposed within the lumen thereof. In this embodiment, swaging the combination of the tubular braid and the inner liner preferably embeds the tubular braid at least at the intersections down into the inner liner which helps to further reduce the wall thickness of the swaged braided catheter. For example, FIG. 10 illustrates a flattened intersection 440 of a tubular braid 432 that has been swaged with the inner liner 434 disposed within a lumen thereof. As shown, a portion of the flattened bottom wire member 438a is embedded within the inner liner 434, thus reducing the thickness of the intersection 440 extending beyond the inner liner 434, and thereby reducing the overall wall thickness of the swaged braided catheter.

The method (400) of FIG. 9 further includes disposing (405) an outer jacket 36 over the tubular braid 32 by any of the methods discussed in more detail above or any other suitable means known by those skilled in the art.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. A catheter comprising:
   a tubular braid having a proximal end a distal end, the tubular braid including a plurality of wire members braided together and a plurality of crossing points defined by crossing wire members of the braided wire members, wherein at each of the crossing points the wire members have a flattened shape and a thickness in the radial dimension, the wire members having a round cross-section having a diameter between the crossing points, such that the thickness of the flattened shape is less than the diameter of the round cross-section.

2. The catheter of claim 1, further comprising an inner liner positioned coaxially within and in contact with the tubular braid, the inner liner defining a lumen of the catheter, the lumen formed through the proximal and distal ends of the tubular braid.

3. The catheter of claim 1, further comprising an outer sleeve positioned coaxially about and in contact with the tubular braid.

4. The catheter of claim 1, wherein the wire members have a round cross-section with a first diameter, wherein the first thickness of the pre-compressed crossing points is equal to two times the first diameter, and wherein the second thickness of the compressed crossing points is approximately equal to one half of the first thickness.

5. The catheter of claim 1, wherein the wire members initially have a round cross-section with a third thickness along each of their lengths such that at a point located between the flattened regions the wire members maintain the initial round cross-section with the third thickness, the wire members having a fourth thickness at the flattened regions, wherein the fourth thickness is less than the third thickness.

6. The catheter of claim 1, further comprising an inner coil shaft positioned coaxially within the tubular braid.

7. The catheter of claim 1, further comprising an outer coil shaft positioned coaxially about the tubular braid.

8. The catheter of claim 1, wherein the wire members are formed from one of stainless steel, tungsten, gold, titanium, silver, copper, platinum, palladium, iridium, ELGILOY nickel-cobalt alloys, cobalt-chrome alloys, molybdenum tungsten alloys, tantalum alloys, titanium alloys, and a mixture thereof.

\* \* \* \* \*